United States Patent
Zhu et al.

US006432973B1

(10) Patent No.: US 6,432,973 B1
(45) Date of Patent: Aug. 13, 2002

(54) WATER SOLUBLE RAPAMYCIN ESTERS

(75) Inventors: Tianmin Zhu, Monroe, NY (US); Mahdi Fawzi, Morristown, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/954,782

(22) Filed: Sep. 18, 2001

Related U.S. Application Data

(60) Provisional application No. 60/233,776, filed on Sep. 19, 2000.

(51) Int. Cl.$^7$ .................... C07D 498/16; C07D 498/18; C07D 491/06; A61K 31/395; A61K 31/445
(52) U.S. Cl. ......................... 514/291; 540/456
(58) Field of Search ........................... 540/456; 514/291

(56) References Cited

U.S. PATENT DOCUMENTS

| | | | |
|---|---|---|---|
| 3,929,992 A | 12/1975 | Sehgal et al. | 424/122 |
| 3,993,749 A | 11/1976 | Sehgal et al. | 424/122 |
| 4,316,885 A | 2/1982 | Rakhit | 424/122 |
| 4,375,464 A | 3/1983 | Sehgal et al. | 424/122 |
| 4,401,653 A | 8/1983 | Eng | 424/114 |
| 4,650,803 A | 3/1987 | Stella et al. | 514/291 |
| 4,885,171 A | 12/1989 | Surendra et al. | 424/122 |
| 5,023,262 A | 6/1991 | Caulfield et al. | 514/291 |
| 5,023,263 A | 6/1991 | Von Burg | 514/291 |
| 5,078,999 A | 1/1992 | Warner et al. | 424/122 |
| 5,080,899 A | 1/1992 | Strum et al. | 424/122 |
| 5,093,338 A | 3/1992 | Byrne et al. | 514/291 |
| 5,093,339 A | 3/1992 | Kasama et al. | 514/291 |
| 5,100,883 A | 3/1992 | Schiehser | 514/183 |
| 5,100,899 A | 3/1992 | Calne | 514/291 |
| 5,102,876 A | 4/1992 | Caulfield | 514/183 |
| 5,118,677 A | 6/1992 | Caufield | 514/183 |
| 5,118,678 A | 6/1992 | Kao et al. | 514/183 |
| 5,120,842 A | 6/1992 | Failli et al. | 540/452 |
| 5,130,307 A * | 7/1992 | Failli et al. | 514/321 |
| 5,151,413 A | 9/1992 | Caufield et al. | 514/63 |
| 5,162,333 A | 11/1992 | Failli et al. | 514/291 |
| 5,177,203 A | 1/1993 | Failli et al. | 540/456 |
| 5,206,018 A | 4/1993 | Sehgal et al. | 424/122 |
| 5,221,670 A * | 6/1993 | Caufield | 514/183 |
| 5,233,036 A | 8/1993 | Hughes | 540/455 |
| 5,256,790 A | 10/1993 | Nelson | 514/291 |
| 5,258,389 A | 11/1993 | Goulet et al. | 514/291 |
| 5,260,300 A | 11/1993 | Hu | 514/291 |
| 5,262,423 A | 11/1993 | Kao | 514/291 |
| 5,286,730 A | 2/1994 | Caufield et al. | 514/291 |
| 5,286,731 A | 2/1994 | Caufield et al. | 514/291 |
| 5,288,711 A | 2/1994 | Mitchell et al. | 514/56 |
| 5,302,584 A | 4/1994 | Kao et al. | 514/80 |
| 5,321,009 A | 6/1994 | Baeder et al. | 514/15 |
| 5,362,718 A | 11/1994 | Skotnicki | 514/63 |
| 5,385,908 A | 1/1995 | Nelson et al. | 514/291 |
| 5,385,909 A | 1/1995 | Nelson et al. | 514/291 |
| 5,385,910 A | 1/1995 | Ocain et al. | 514/291 |
| 5,387,589 A | 2/1995 | Kulkarni | 514/291 |
| 5,389,639 A | 2/1995 | Failli et al. | 514/291 |
| 5,391,730 A | 2/1995 | Skotnicki et al. | 540/456 |
| 5,411,967 A | 5/1995 | Kao et al. | 514/291 |
| 5,434,260 A | 7/1995 | Skotnicki et al. | 514/291 |
| 5,463,048 A | 10/1995 | Skotnicki et al. | 540/456 |
| 5,480,988 A | 1/1996 | Failli et al. | 540/456 |
| 5,480,989 A | 1/1996 | Kao et al. | 540/456 |
| 5,489,680 A | 2/1996 | Failli et al. | 540/456 |
| 5,491,231 A | 2/1996 | Nelson et al. | 540/456 |
| 5,496,832 A | 3/1996 | Armstrong | 514/291 |
| 5,504,091 A | 4/1996 | Molnar-Kimber | 514/291 |
| 5,516,770 A | 5/1996 | Waranis et al. | 514/183 |
| 5,516,781 A | 5/1996 | Morris et al. | 514/291 |
| 5,530,006 A | 6/1996 | Waranis et al. | 514/291 |
| 5,536,729 A | 7/1996 | Waranis et al. | 514/291 |
| 5,559,121 A | 9/1996 | Harrison et al. | 514/291 |
| 5,561,138 A | 10/1996 | Armstrong | 514/291 |
| 5,616,588 A | 4/1997 | Waranis et al. | 514/291 |
| 5,665,772 A | 9/1997 | Cottens et al. | 514/514 |
| 5,780,462 A * | 7/1998 | Lee et al. | 514/183 |
| 5,985,325 A | 11/1999 | Nagi | 424/482 |
| 5,989,591 A | 11/1999 | Nagi | 424/493 |

FOREIGN PATENT DOCUMENTS

| | | | |
|---|---|---|---|
| EP | 0 525 960 A1 | | 2/1993 |
| EP | 781 776 | * | 7/1997 |
| WO | WO 94/25072 | * | 11/1994 |

OTHER PUBLICATIONS

C.V. Vezina et al., J. Anitbiot., 1975, 721,28.
H.A. Baker et al., J. Antibiot., 1978, 539,31.
FASEB, 1989, 3411,3.
FASEB, 1989, 5256,3.
R.Y. Calne et al., Lancet, 1978, 1183.
R. Martel et al., Can. J. Physiol. Pharmacol., 1977, 48, 55.
T. Matsumoto et al., Atheroschlerosis, 1998, 95, 139.
S.E. Roselaar et al., J. Clin. Invest., 1995, 1906, 96.
K.B. Lemstrom et al., Arterioscler. Thomb. Vasc. Biol. 1996, 553, 16(4).
T. Quaschning et al., Kidney Int., 1999, S235, 56(71).
E.E. Emeson et al., Am. J. Pathol., 1993, 1906, 142(6).
J. Gibbons et al., Proc. Am. Assoc. Can. Res., 1999, 301, 40.
B. Geoerger et al., Proc. Am. Assoc. Can. Res., 1999, 603, 40.
J. Alexandre, Bull. Cancer, 1999, 808–811, 86.
J. Alexandre et al., Clin. Cancer Res., 1999, Abstract 7, Nov. Suppl.

* cited by examiner

*Primary Examiner*—Bruck Kifle
(74) *Attorney, Agent, or Firm*—Arnold S. Milowsky

(57) ABSTRACT

This invention provide pegylated hydroxyesters of rapamycin which are useful in inducing immunosuppression and in the treatment of transplantation rejection, autoimmune diseases, solid tumors, fungal infections, and vascular disease.

18 Claims, No Drawings

WATER SOLUBLE RAPAMYCIN ESTERS

This application claims priority from provisional application Ser. No. 60/233,776, filed Sep. 19, 2000, the entire disclosure of which is hereby incorporated by reference.

BACKGROUND OF THE INVENTION

This invention relates to water soluble rapamycin esters which are useful in inducing immunosuppression and in the treatment of transplantation rejection, autoimmune diseases, solid tumors, fungal infections, and vascular disease. More particularly, this invention concerns methoxypoly(ethylene glycol) esters of hydroxyesters of rapamycin and methods for using them for inducing immunosuppression, and in the treatment of transplantation rejection, graft vs. host disease, autoimmune diseases, diseases of inflammation, adult T-cell leukemia/lymphoma, solid tumors, fungal infections, cardiovascular disease, cerebral vascular disease, peripheral vascular disease or hyperproliferative vascular disorders.

Rapamycin is a macrocyclic triene antibiotic produced by *Streptomyces hygproscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Caine et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

A rapamycin ester, rapamycin 42-ester with 3-hydroxy-2-(hydroxymethyl)-2-methylpropionic acid [disclosed in U.S. Pat. No. 5,362,718], also known as CCI-779, has been shown to have antitumor activity against a variety of tumor cell lines, in in vivo animal tumor models, and in Phase I clinical trials. [Gibbons, J., Proc. Am. Assoc. Can. Res. 40: 301 (1999); Geoerger, B., Proc. Am. Assoc. Can. Res. 40: 603 (1999); Alexandre, J., Proc. Am. Assoc. Can. Res. 40: 613 (1999); and Alexandre, J., Clin. Cancer. Res. 5 (November Supp.): Abstr. 7 (1999)].

Polyethylene glycol (PEG) is a linear or branched, neutral polymer available in a variety of molecular weights and is soluble in water and most organic solvents. At molecular weights less than 1000 are the viscous, colorless liquids; higher molecular weight PEGs are waxy, white solids. The melting point of the solid is proportional to the molecular weight, approaching a plateau at 67° C. Molecular weight range from a few hundred to approximately 20,000 are commonly used in biological and biotechnological applications. Of much interest in the biomedical areas is the fact that PEG is nontoxic and was approved by FDA for internal consumption. Peglyated rapamycin is disclosed in US Pat. No. 5,780,462.

DESCRIPTION OF THE INVENTION

This invention provides methoxypoly(ethylene glycol) esters of hydroxyesters of rapamycin having the structure

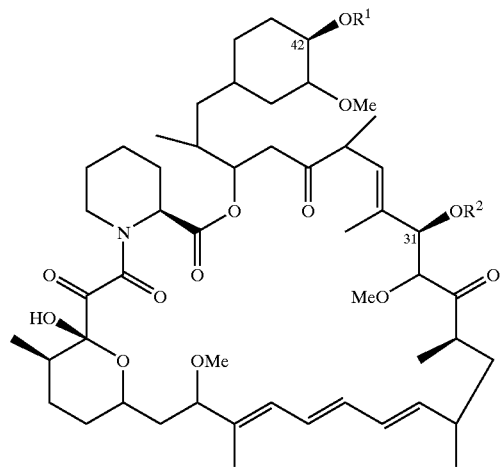

wherein $R^1$ and $R^2$ are each, independently, hydrogen or —CO$(CR^3R^4)_b(CR^5R^6)_dCR^7R^8R^9$;

$R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;

$R^5$ and $R^6$ are each, independently, hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

$R^7$ is hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

$R^8$ and $R^9$ are each, independently, hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

$R^{10}$ is hydrogen or —COCH$_2$—S—CH$_2$CH$_2$—(O—CH$_2$—CH$_2$)$_n$—OCH$_3$;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that $R^1$ and $R^2$ are both not hydrogen and further provided that either $R^1$ or $R^2$ contains at least one —(CR$^3$R$^4$)$_f$OR$^{10}$ group in which $R^{10}$ is —COCH$_2$—S—CH$_2$CH$_2$—(O—CH$_2$—CH$_2$)$_n$—OCH$_3$, or a pharmaceutically acceptable salt thereof which are useful for inducing immunosuppression, and in the treatment of transplantation rejection, graft vs. host disease, autoimmune diseases, diseases of inflammation, adult T-cell leukemia/lymphoma, solid tumors, fungal infections, cardiovascular disease, cerebral vascular disease, peripheral vascular disease or hyperproliferative vascular disorders. The compounds of this invention can also be referred to as pegylated hydroxyesters of rapamycin.

When applicable, pharmaceutically acceptable salts can be formed from organic and inorganic bases (i.e., when a compound contains a free hydroxyl group), such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when the rapamycin or antiestrogen contains a suitable acidic moiety.

As used in accordance with this invention, the term "providing," with respect to providing a compound or substance covered by this invention, means either directly administering such a compound or substance, or administering a prodrug, derivative, or analog which will form the equivalent amount of the compound or substance within the body.

Of the pegylated hydroxyesters of rapamycin covered by this invention, it is preferred that the hydroxyester of rapamycin is CCI-779, in which one or both of the hydroxyl groups of the 3-hydroxy-2-(hydroxymethyl)-2-methylpropionic acid moiety are pegylated. Of the compounds of this invention, it is preferred that n=5–200; more preferred that n=8–135. Most preferred members are those in which n=8–20 and those in which n=90–120. The values of n refer to the range of repeating ethoxy units in the PEG side chain. For example, when a compound is described as having n=5–200, it means that such compound consists of a mixture of compounds having a normal distribution between n=5 and n=200, with approximately n=100 having the greatest frequency. With compounds III and IV, the average n was 108, and 99% of n being between 65 and 155. The compounds of this invention may also be described and understood based upon the average molecular weight of the polyethylene glycol chains used to produce their ester chains. For instance, an CCl-779-PEG 5000 ester refers to a compound of the general formula above in which one side chain PEG ester is formed utilizing a polyethylene glycol derivative having an average molecular weight range at or near 5,000; and CCl-779-(PEG 5000)$_2$ ester refers to a compound of the general formula above in two side chain PEG esters are formed utilizing a polyethylene glycol derivative having an average molecular weight range at or near 5,000.

The reagents used in the preparation of the compounds of this invention can be either commercially obtained or can be prepared by standard procedures described in the literature.

The preparation of the hydroxyesters of rapamycin, from which the pegylated hydroxyesters are made from, are described in U.S. Pat. No. 5,362,718, which is hereby incorporated by reference. One or more of the hydroxyesters may be acylated with a acylating agent having the general structure X-CH$_2$CO$_2$H, where X is a suitable leaving group, such as bromine or iodine, in the presence of a coupling agent such as dicyclohexylcarbodiimide (DCC) in the presence of a base catalyst, such as dimethylaminopyridine (DMAP). Accordingly, rapamycin 42-ester with 3-hydroxy-2-(2-iodo-acetoxymethyl)-2-methyl-propionic acid (Compound I) and rapamycin 42-ester with 3-(2-Iodo-acetoxy)-2-(2-iodo-acetoxymethyl)-2-methyl-propionic acid (Compound II) are intermediates prepared using this methodology, that are useful in the production of the corresponding pegylated hydroxyesters of rapamycin (Compounds III and IV, respectively).

The pegylated esters may be produced utilizing the polyethylene glycols known in the art, such as those described on pages 355 to 361 of the Handbook of Pharmaceutical Excipients, Second Edition, 1994. The preferred compounds of this invention may also be described as those of the formula esterified using polyethylene glycols having an average molecular weight of from about 200 to about 200,000. A preferred range of the PEG esters of this invention includes those in which the molecular weight of the polyethylene glycol portion of the ester chain has a molecular weight in the range of from about 300 to about 20,000, more preferably between about 350 and about 6,000. Reaction of the hydroxyester of rapamycin which has been acylated as described above, with a suitable polyethyleneglycol thiol in the presence of a base, such as sodium bicarbonate provides the desired pegylated hydroxyester of rapamycin.

The antitumor activity of the compounds of this invention were confirmed in a standard pharmacological test procedure which measures the inhibition of U87MG human glioblastoma cell growth (as a function of $^3$H-thymidine incorporation), using CCl-779-PEG 5000 ester (Compound III) and CCl-779-(PEG 5000)$_2$ ester (Compound IV) as representative compounds of this invention. The following briefly describes the procedure used and results obtained. U87MG human glioblastoma cells (ATCC #HTB-14; available from the American Type Culture Collection; 10801 University Boulevard; Manassas, Va. 20110;), were grown in the following media.

Growth Medium: BRL Minimum Essential Medium with Earle Salts (500 mL)
+5 mL BRL MEM Non-Essential Amino Acids (10 mM)
+5 mL BRL Penicillin-Streptomycin (100000 u/mL, 10000 µg/mL)
+5 mL BRL Na Pyruvate Solution (100 mM)
+5 mL BRL L-Glutamine 200 mM
+50 mL BRL Fetal Bovine Serum (Qualified)

Test Procedure:

1. Cells were trypsinized and plated at a concentration of $10^4$ cells/well in a final volume of 200 µL growth medium in 96-well flat bottom plates and allowed to adhere for 24 hours at 37° C.

2. The media was removed by aspiration with care to not disturb the cell monolayer. 200 µL of fresh growth media was added per well, allowing enough wells for samples to be run in triplicate. Test compounds were added in 10 µL phosphate buffer solution (PBS) and incubated for another 48 hours at 37° C.

3. During the last 5 hours of incubation, plates were labeled with 1 µCi $^3$H thymidine per well. (New England Nuclear thymidine, catalog #NET-027, 6.7 Ci/mmole). The 1 µCi was added in 10 µL of PBS (on the day of harvest). The plates were returned to the incubator for the last 5 hours.

4. The radioactive media was removed by aspiration, with care not to disturb the cell monolayer. Then 50 µL of BRL 10X Trypsin was added to each well, followed by incubation at 37° C. for 10 minutes or until the monolayer was loosened from the well bottom. Samples were harvested on a glass fiber filter mat using a Skatron 96 well harvester. Mats were counted in a Wallac Betaplate counter.

| Results: | |
| --- | --- |
| Compound | IC$_{50}$ |
| CCI-779 | 0.6 ng/mL |
| Compound III | 1.0 ng/mL* |
| Compound IV | 4.0 ng/mL* |

*ng/mL equivalent of CCI-779

The results obtained in this standard pharmacological test procedure show that the compounds of this invention inhibit tumor cell growth and are therefore useful as antineoplastic agents. In particular, the compounds of this invention are useful in treating or inhibiting the growth of solid tumors, including sarcomas and carcinomas, such as astrocytomas, prostate cancer, breast cancer, small cell lung cancer, and ovarian cancer.

The compounds of this invention are also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; adult T-cell leukemia/lymphoma; fungal infections; hyperproliferative vascular diseases such as restenosis; graft vascular atherosclerosis; and cardiovascular disease, cerebral vascular disease, and peripheral vascular disease, such as coronary artery disease, cerebrovascular disease, arteriosclerosis, atherosclerosis, nonatheromatous arteriosclerosis, or vascular wall damage from cellular events leading toward immune mediated vascular damage, and inhibiting stroke or multiinfarct dementia.

When used for restenosis, it is preferred that the compounds of this invention are used to treat restenosis that occurs following an angioplasty procedure. When used for this treating restenosis following an angioplasty, the compounds of this invention can be administered prior to the procedure, during the procedure, subsequent to the procedure, or any combination of the above.

This invention also covers analogous pegylated hydroxyesters of other rapamycins known in the art such as, but not limited to, 29-demethoxyrapamycin, [U.S. Pat. No. 4,375,464, 32-demethoxyrapamycin under C. A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C. A. nomenclature]; 7,29-bisdesmethylrapamycin [U.S. Pat. No. 5,093,338, 7,32-desmethylrapamycin under C. A. nomenclature]; 27-hydroxyrapamycin [U.S. Pat. No. 5,256,790] and 15-hydroxyrapamycin [U.S. Pat. No. 5,102,876]. This invention also covers esters at the 31-position of 42-oxorapamycin [U.S. Pat. No. 5,023,263]. The disclosures in the above cited U.S. Pat. Nos. are hereby incorporated by reference.

When administered for the treatment or inhibition of a particular disease state or disorder, it is understood that the effective dosage of the pegylated hydroxyester of rapamycin may vary depending upon the particular compound utilized, the mode of administration, the condition, and severity thereof, of the condition being treated, as well as the various physical factors related to the individual being treated. As used in accordance with invention, satisfactory results may be obtained when the pegylated hydroxyester of rapamycin is administered in a daily oral dosage of from about projected daily dosages of active compound would be 0.1 µg/kg–100 mg/kg, preferably between 0.001–25 mg/kg, and more preferably between 0.01–5 mg/kg. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. The pegylated esters of this invention provide an advantage in ease of formulation and administration over the non-pegylated esters of rapamycin, in that they are significantly more water soluble than corresponding non-pegylated esters. For example, both compounds 3 and 4 had a water solubility of >100 mg/mL, whereas CCl-779 had a water solubility of <1.1 µg/mL. This advantage is particularly important for oral and parenteral administration.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound (s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic. absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The preparation of representative examples of this invention is described below.

EXAMPLE 1

Preparation of Rapamycin 42-Ester with 3-Hydroxy-2-(2-iodo-acetoxymethyl)-2-methyl-propionic Acid (Compound I) and Rapamycin 42-Ester with 3-(2-Iodo-acetoxy)-2-(2-iodo-acetoxymethyl)-2-methyl-propionic Acid (Compound II)

Compound I

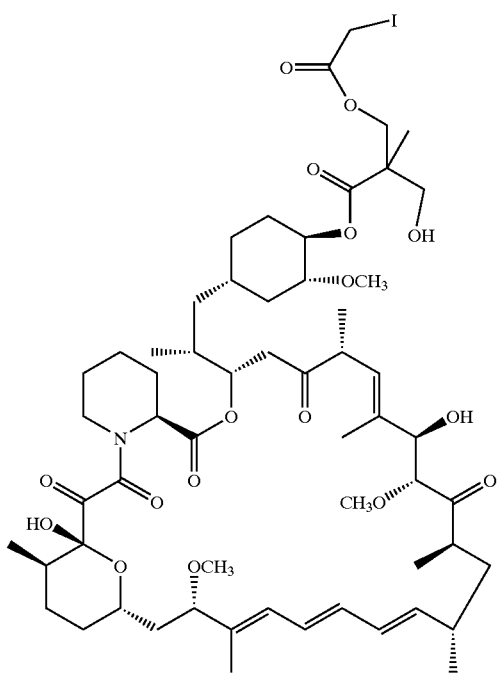

Compound II

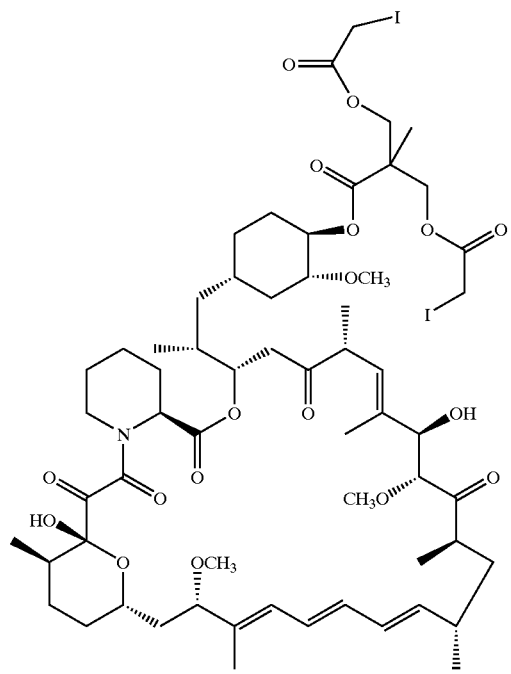

CCl-779 (1.03 g 1.0×10$^{-3}$ mole), 4-Dimethylaminopyridine (3.0 mg) and 1,3-Dicyclohexylcarbodiimide (0.136 g, 6.6×10$^{-4}$ mole) were dissolved in 50 mL anhydrous methylene chloride in a 250 mL round-bottom flask. Iodoacetic acid (0.185 g, 1.0×10$^{-3}$ mole) was dissolved in 10 mL anhydrous methylene chloride. The iodoacetic acid solution was added into reaction mixture over a period of 10 min with stirring by a magnetic bar. Then the reaction mixture was stirred at room temperature for another 2.5 h. The solution was then filtered through a filter paper. The filtrate was transferred to a separatory funnel, washed 50 mL of sodium bicarbonate solution (5.5 g/100 mL) and then washed with 2×50 mL of water. The methylene chloride layer was dried with 10 g anhydrous sodium sulfate for 2 h. Then sodium sulfate was filtered out and methylene chloride was removed by rotary evaporation. A total of 0.93 g yellow solid was obtained. Isolation of pure compound I and compound II was performed by preparative HPLC on a Prep Nova-pak HR C18 (300×19 mm) column from Waters. Compound I eluted at 18.4 min and compound 11 eluted at 24.4 min using a gradient (30% A, 70% B for 5 min. then to 100% B in 30 min.). A is 90% water, 10% acetonitrile; B is 10% water, 90% acetonitrile. The fraction was collected and extracted by 2×100 ml methylene chloride. The organic layer was combined and dried with anhydrous sodium sulfate for 4 h. The organic solvent was removed by rotary evaporation to dryness. Compound I, a yellowish solid was obtained (0.14 g). $^1$H NMR (CDCL$_3$, 400 MHz) δ 3.68 (s, 2H, I—CH$_2$—CO$_2$—), 4.28 (dd, 2H, —CO$_2$—CH$_2$—). MS m/z 1215.8 (M+NH$_4$)$^+$. Compound II, a yellowish solid was obtained (0.08 g). $^1$H NMR (CDCL$_3$, 400 MHz) δ 3.72 (s, 4H, 2×I—CH$_2$—CO$_2$—), 4.28 (dd, 4H, 2×—CO$_2$—CH$_2$—). MS m/z 1383.6 (M+NH$_4$)$^+$.

EXAMPLE 2

Preparation of CCl-779-PEG 5000—Rapamycin 42-Ester with 3-Hydroxy-2-(hydroxymethyl)-2-methylpropionic Acid Methoxypoly(ethylene glycol)thiol 5000 Conjugate (Compound III)

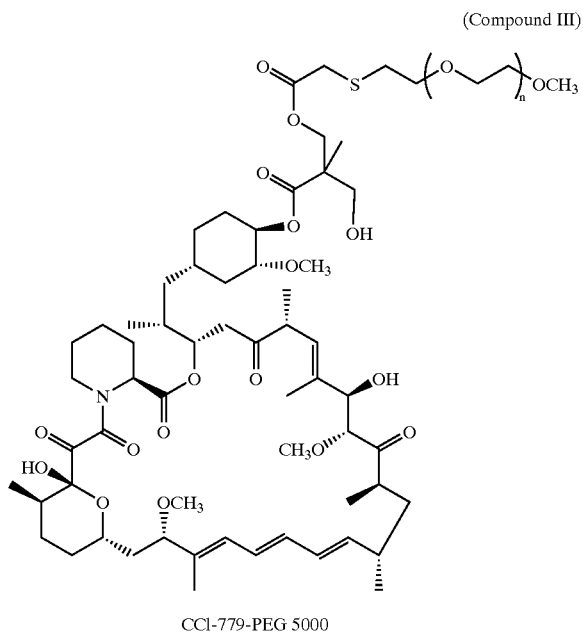

(Compound III)

CCl-779-PEG 5000
with average $n$ = 108

Compound I (90 mg, $7.6 \times 10^{-5}$ mole) was dissolved in 40 mL of solution containing 50% acetonitrile and 50% aqueous $NaHCO_3$ (0.1 M) solution. The solution was flushed with $N_2$ for 10 min. The original sample 10 μL was taken for HPLC analysis. Then mPEG-SH 5000 (450 mg, $9.1 \times 10^{-5}$ mole) was added to the reaction solution and the reaction mixture was stirred at room temperature for another 45 min. The reaction was checked again by taking 10 μL sample for HPLC analysis. The chromatogram showed that compound I was 100% converted to Compound III. The reaction mixture was extracted with 2×100 mL methylene chloride. The organic layer was dried with anhydrous sodium sulfate then filtered. The filtrate was concentrated to a volume of 20 mL by rotaty evaporation. The crude product was precipitated out after adding 150 mL ether. A total of 404 mg white powder was obtained after filtered out by a sintered glass funnel and dried under vacuum. Isolation of pure compound III, which may also be referred to as CCl-779-PEG 5000, was performed by preparative HPLC on a Prep Nova-pak HR C18 (300×19 mm) column from Waters. Compound III eluted at 18 min using a gradient (60% A, 40% B for 5 min then at 20% A, 80% B in 30 min). The fraction was collected and extracted by 2×100 mL methylene chloride. The organic layer was combined and dried with anhydrous sodium sulfate for 4 hr. The organic solvent was removed by rotary evaporation to dryness. The residue was dissolved in 5 mL methylene chloride and was precipitated out after adding 150 mL ether. A white powder was obtained after filtered out by a sintered glass funnel and dried under vacuum. $^1H$ NMR ($CDCl_3$, 400 MHz) δ 2.83 (t, 2H, —S—$CH_2$—$CH_2$—), 3.30 (s, 2H, —CO—$CH_2$—S), 3.38 (s, 3H, —$OCH_3$), 4.25 (dd, 2H, —$CO_2$—$CH_2$—). MS (MALD/TOF) m/z 5894.5 (ave. M. Wt.) which indicate the average n=108 for compound III, with 99% of n being between 65 and 155.

EXAMPLE 4

Preparation of CCl-779-(PEG 5000)$_2$—Rapamycin 42-Ester with 3-Hydroxy-2-(hydroxymethyl)-2-methylpropionic Acid bis(Methoxypoly(ethylene glycol)thiol 5000) Conjugate (Compound IV)

(Compound IV)

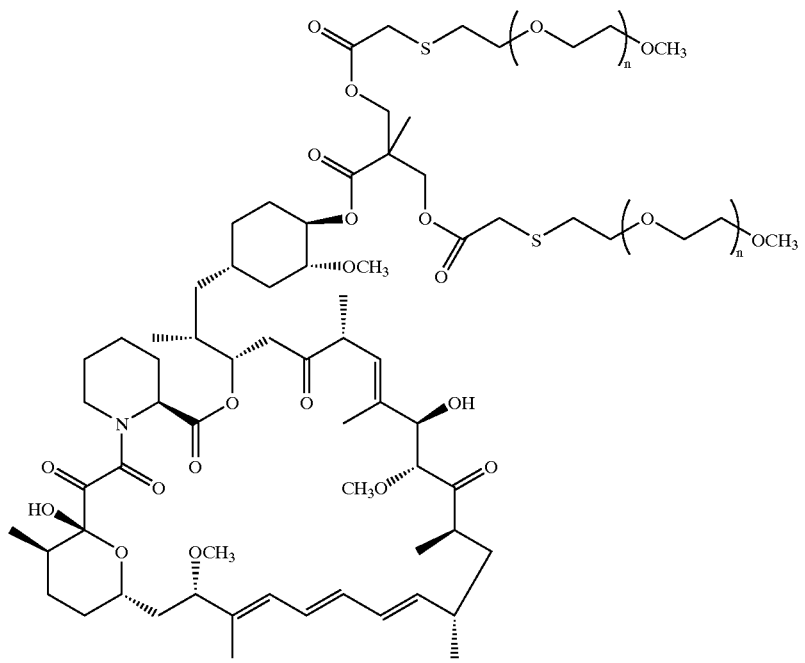

CCl-779-(PEG 5000)2
with average $n$ = 108

Compound II (50 mg, 3.6×10⁻⁵ mole) was dissolved in 30 mL of solution containing 50% acetonitrile and 50% aqueous $NaHCO_3$ (0.1 M) solution. The solution was flushed with $N_2$ for 10 min. The original sample 10 μL was taken for HPLC analysis. Then mPEG-SH 5000 (500 mg, 1.0×10⁻⁴ mole) was added to the reaction solution and the reaction mixture was stirred at room temperature for about 70 min. The reaction was checked again by taking 10 μL sample for HPLC analysis. The chromatogram showed that compound II was 100% converted to Compound IV. The reaction mixture was extracted with 2×50 mL methylene chloride. The organic layer was dried with anhydrous sodium sulfate then filtered. The filtrate was concentrated to a volume of 10 mL by rotaty evaporation. The crude product was precipitated out after adding 150 mL ether. A total of 500 mg white powder was obtained after filtered out by a sintered glass funnel and dried under vacuum. Isolation of pure compound IV, which may also be referred to as CCl-779-(PEG 5000)$_2$, was performed by preparative HPLC on a Prep Nova-pak HR C18 (300×19 mm) column from Waters. Compound IV eluted at 22 min using a gradient (60% A, 40% B for 5 min then at 20% A, 80% B in 30 min). The fraction was collected and extracted by 2×100 mL methylene chloride. The organic layer was combined and dried with anhydrous sodium sulfate for 4 hr. The organic solvent was removed by rotary evaporation to dryness. The residue was dissolved in 5 mL methylene chloride and was precipitated out after adding 150 mL ether. A white powder was obtained after filtered out by a sintered glass funnel and dried under vacuum. ¹H NMR ($CDCl_3$, 400 MHz) δ 2.81 (t, 4H, 2×S—$CH_2$—$CH_2$—), 3.29 (s, 4H, 2×CO—$CH_2$—S—), 3.38 (s, 6H, 2×$OCH_3$), 4.26 (dd, 4H, 2×—$CO_2$—$CH_2$—). MS (MALD/TOF) m/z 10760.7 (ave. M. Wt.) which indicate the average n=108 for compound IV, with 99% of n being between 65 and 155.

What is claimed is:

1. A compound having the structure

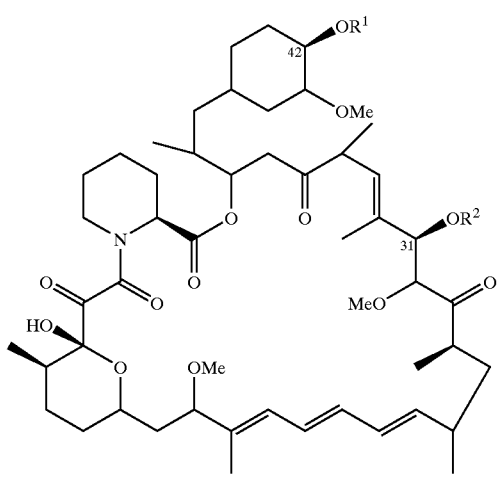

wherein
 $R^1$ and $R^2$ are each, independently, hydrogen or —CO$(CR^3R^4)_b(CR^5R^6)_dCR^7R^8R^9$;
 $R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;
 $R^5$ and $R^6$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;
 $R^7$ is hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;
 $R^{10}$ is hydrogen or —$COCH_2$—S—$CH_2CH_2$—(O—$CH_2$—$CH_2$)$_n$—$OCH_3$;
 $R^{11}$ is hydrogen, alkyl of 1–6 carbon atoms, alkenyl of 2–7 carbon atoms, alkynyl of 2–7 carbon atoms, or phenylalkyl of 7–10 carbon atoms;
 b=0–6;
 d=0–6;
 f=0–6;
 n=5–450;

with the proviso that $R^1$ and $R^2$ are both not hydrogen and further provided that either $R^1$ or $R^2$ contains at least one —$(CR^3R^4)_fOR^{10}$ group in which $R^{10}$ is —$COCH_2$—S—$CH_2CH_2$—(O—$CH_2$—$CH_2$)$_n$—$OCH_3$, or a pharmaceutically acceptable salt thereof.

2. The compound of claim 1, wherein $R^2$ is hydrogen.
3. The compound of claim 2, wherein n=5–200.
4. The compound of claim 3, wherein n=8–135.
5. The compound of claim 4, wherein n=8–20.
6. The compound of claim 4, wherein n=90–120.
7. The compound of claim 1, which is rapamycin 42-ester with 3-hydroxy-2-(hydroxymethyl)-2-methylpropionic acid methoxypoly(ethylene glycol)thiol 5000 conjugate.
8. The compound of claim 1, which is rapamycin 42-ester with 3-hydroxy-2-(hydroxymethyl)-2-methylpropionic acid bis(methoxypoly(ethylene glycol)thiol 5000 conjugate.
9. A method of treating or inhibiting transplant rejection or graft vs. host disease in a mammal in need thereof, which comprises providing to said mammal an effective amount of a compound having the structure

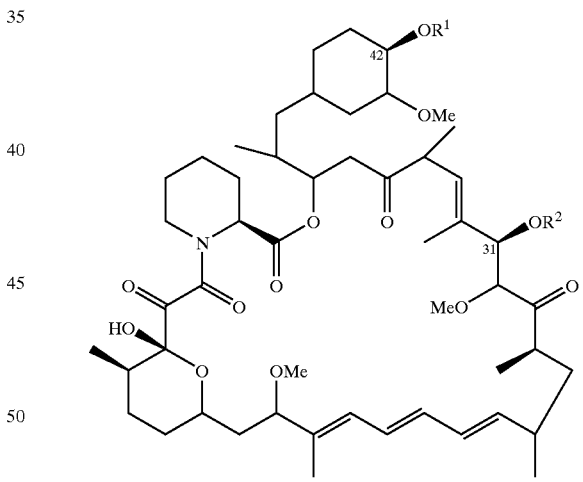

wherein
 $R^1$ and $R^2$ are each, independently, hydrogen or —CO$(CR^3R^4)_b(CR^5R^6)_dCR^7R^8R^9$;
 $R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;
 $R^5$ and $R^6$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;
 $R^7$ is hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^{10}$ is hydrogen or —$COCH_2$—S—$CH_2CH_2$—(O—$CH_2$—$CH_2)_n$—$OCH_3$;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that $R^1$ and $R^2$ are both not hydrogen and further provided that either $R^1$ or $R^2$ contains at least one —$(CR^3R^4)_fOR^{10}$ group in which $R^{10}$ is —$COCH_2$—S—$CH_2CH_2$—(O—$CH_2$—$CH_2)_n$—$OCH_3$, or a pharmaceutically acceptable salt thereof.

10. A method of treating or inhibiting a solid tumor selected from the group consisting of astrocytoma, prostate cancer, breast cancer, small cell lung cancer, and ovarian cancer in a mammal in need thereof, which comprises providing to said mammal a compound having the structure

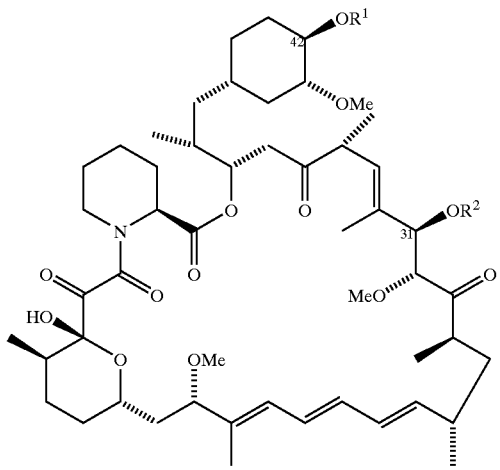

wherein $R^1$ and $R^2$ are each, independently, hydrogen or —CO$(CR^3R^4)_b(CR^5R^6)_dCR^7R^8R^9$;

$R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;

$R^5$ and $R^6$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^7$ is hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^{10}$ is hydrogen or —$COCH_2$—S—$CH_2CH_2$—(O—$CH_2$—$CH_2)_n$—$OCH_3$;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that $R^1$ and $R^2$ are both not hydrogen and further provided that either $R^1$ or $R^2$ contains at least one —$(CR^3R^4)_fOR^{10}$ group in which $R^{10}$ is —$COCH_2$—S—$CH_2CH_2$—(O—$CH_2$—$CH_2)_n$—$OCH_3$, or a pharmaceutically acceptable salt thereof.

11. A method of treating or inhibiting a fungal infection in a mammal in need thereof, which comprises providing to said mammal an effective amount of a compound having the structure

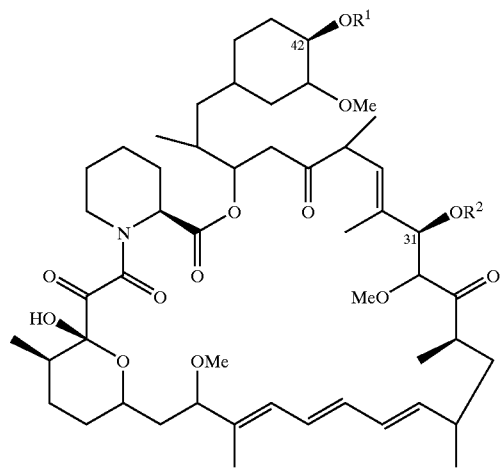

wherein $R^1$ and $R^2$ are each, independently, hydrogen or —CO$(CR^3R^4)_b(CR^5R^6)_dCR^7R^8R^9$;

$R^3$ and $R^4$ are each, independently, hydrogen, alkyl of 1–6 carbon atoms, alkenyl of 2–7 carbon atoms, alkynyl of 2–7 carbon atoms, trifluoromethyl, or —F;

$R^5$ and $R^6$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^7$ is hydrogen, alkyl of 1–6 carbon atoms, alkenyl of 2–7 carbon atoms, alkynyl of 2–7 carbon atoms, —$(CR^3R^4)_fOR10$, —$CF_3$, —F, or—$CO_2R^{11}$;

$R^8$ and $R^9$ are each, independently, hydrogen, alkyl of 1–6 carbon atoms, alkenyl of 2–7 carbon atoms, alkynyl of 2–7 carbon atoms, —$(CR^3R^4)_fOR^{10}$, —$CF_3$, —F, or —$CO_2R^{11}$;

$R^{10}$ is hydrogen or —$COCH_2$—S—$CH_2CH_2$—(O—$CH_2$—$CH_2)_n$—$OCH_3$;

$R^{11}$ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that $R^1$ and $R^2$ are both not hydrogen and further provided that either $R^1$ or $R^2$ contains at least one —$(CR^3R^4)_fOR^{10}$ group in which $R^{10}$ is —$COCH_2$—S—$CH_2CH_2$—(O—$CH_2$—$CH_2)_n$—$OCH_3$, or a pharmaceutically acceptable salt thereof.

12. A method of treating or inhibiting rheumatoid arthritis in a mammal in need thereof, which comprises providing to said mammal an effective amount of a compound having the structure

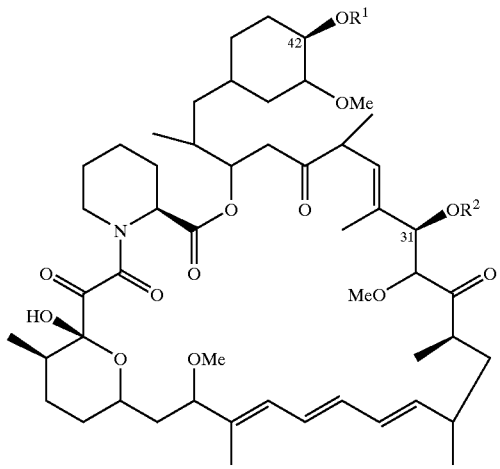

wherein

R$^1$ and R$^2$ are each, independently, hydrogen or —CO(CR$^3$R$^4$)$_b$(CR$^5$R$^6$)$_d$CR$^7$R$^8$R$^9$;

R$^3$ and R$^4$ are each, independently, hydrogen, alkyl of 1–6 carbon atoms, alkenyl of 2–7 carbon atoms, alkynyl of 2–7 carbon atoms, trifluoromethyl, or —F;

R$^5$ and R$^6$ are each, independently, hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

R$^7$ is hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

R$^8$ and R$^9$ are each, independently, hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

R$^{10}$ is hydrogen or —COCH$_2$—S—CH$_2$CH$_2$—(O—CH$_2$—CH$_2$)$_n$—OCH$_3$;

R$^{11}$ is hydrogen, alkyl of 1–6 carbon atoms, alkenyl of 2–7 carbon atoms, alkynyl of 2–7 carbon atoms, or phenylalkyl of 7–10 carbon atoms;

b=0–6;

d=0–6;

f=0–6;

n=5–450;

with the proviso that R$^1$ and R$^2$ are both not hydrogen and further provided that either R$^1$ or R$^2$ contains at least one —(CR$^3$R$^4$)$_f$OR$^{10}$ group in which R$^{10}$ is —COCH$_2$—S—CH$_2$CH$_2$—(O—CH$_2$—CH$_2$)$_n$—OCH$_3$, or a pharmaceutically acceptable salt thereof.

13. A method of treating or inhibiting multiple sclerosis in a mammal in need thereof, which comprises providing to said mammal an effective amount of a compound having the structure

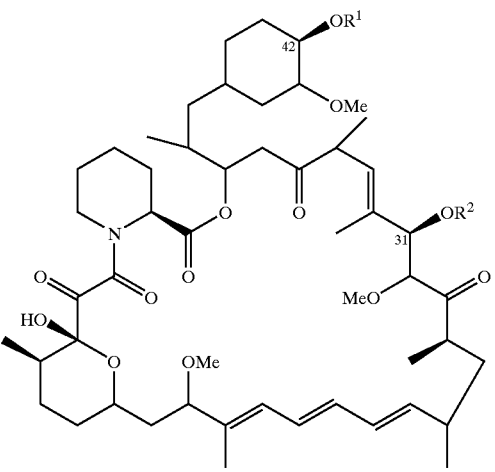

wherein

R$^1$ and R$^2$ are each, independently, hydrogen or —CO(CR$^3$R$^4$)$_b$(CR$^5$R$^6$)$_d$CR$^7$R$^8$R$^9$;

R$^3$ and R$^4$ are each, independently, hydrogen, alkyl of 1–6 carbon atoms, alkenyl of 2–7 carbon atoms, alkynyl of 2–7 carbon atoms, trifluoromethyl, or —F;

R$^5$ and R$^6$ are each, independently, hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

R$^7$ is hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

R$^8$ and R$^9$ are each, independently, hydrogen, alkyl of 1–6 carbon atoms, alkenyl of 2–7 carbon atoms, alkynyl of 2–7 carbon atoms, —(CR$^3$R$^4$)$_f$OR$^{10}$, —CF$_3$, —F, or —CO$_2$R$^{11}$;

R$^{10}$ is hydrogen or —COCH$_2$—S—CH$_2$CH$_2$—(O—CH$_2$—CH$_2$)$_n$—OCH$_3$;

R$^{11}$ is hydrogen, alkyl of 1–6 carbon atoms, alkenyl of 2–7 carbon atoms, alkynyl of 2–7 carbon atoms, or phenylalkyl of 7–10 carbon atoms;

b=0–6;

d=0–6;

f=0–6;

n=5–450;

with the proviso that R$^1$ and R2 are both not hydrogen and further provided that either R$^1$ or R$^2$ contains at least one —(CR$^3$R$^4$)$_f$OR$^{10}$ group in which R$^{10}$ is —COCH$_2$—S—CH$_2$CH$_2$—(O—CH$_2$—CH$_2$)$_n$—OCH$_3$, or a pharmaceutically acceptable salt thereof.

14. A method of treating or inhibiting restenosis in a mammal in need thereof, which comprises providing to said mammal an effective amount of a compound having the structure

17

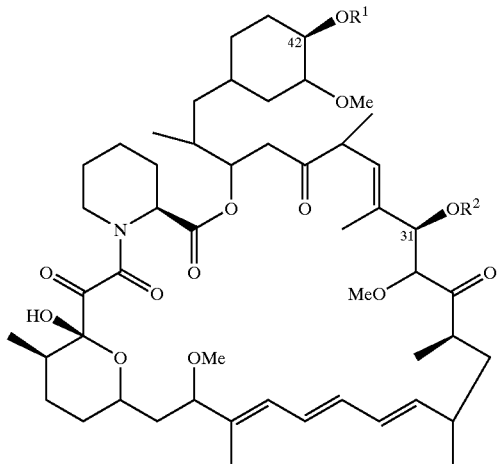

wherein

R¹ and R² are each, independently, hydrogen or —CO(CR³R⁴)_b(CR⁵R⁶)_dCR⁷R⁸R⁹;

R³ and R⁴ are each, independently, hydrogen, alkyl of 1–6 carbon atoms, alkenyl of 2–7 carbon atoms, alkynyl of 2–7 carbon atoms, trifluoromethyl, or —F;

R⁵ and R⁶ are each, independently, hydrogen, alkyl of 1–6 carbon atoms, alkenyl of 2–7 carbon atoms, alkynyl of 2–7 carbon atoms, —(CR³R⁴)_fOR¹⁰, —CF₃, —F, or —CO₂R¹¹;

R⁷ is hydrogen, alkyl of 1–6 carbon atoms, alkenyl of 2–7 carbon atoms, alkynyl of 2–7 carbon atoms, —(CR³R⁴)_fOR¹⁰, —CF₃, —F, or —CO₂R¹¹;

R⁸ and R⁹ are each, independently, hydrogen, alkyl of 1–6 carbon atoms, alkenyl of 2–7 carbon atoms, alkynyl of 2–7 carbon atoms, —(CR³R⁴)_fOR¹⁰, —CF₃, —F, or —CO₂R¹¹;

R¹⁰ is hydrogen or —COCH₂—S—CH₂CH₂—(O—CH₂—CH₂)_n—OCH₃;

R¹¹ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that R¹ and R² are both not hydrogen and further provided that either R¹ or R² contains at least one —(CR³R⁴)_fOR¹⁰ group in which R¹⁰ is —COCH₂—S—CH₂CH₂—(O—CH₂—CH₂)_n—OCH₃, or a pharmaceutically acceptable salt thereof.

15. A method of treating or inhibiting pulmonary inflammation in a mammal in need thereof, which comprises providing to said mammal an effective amount of a compound having the structure

18

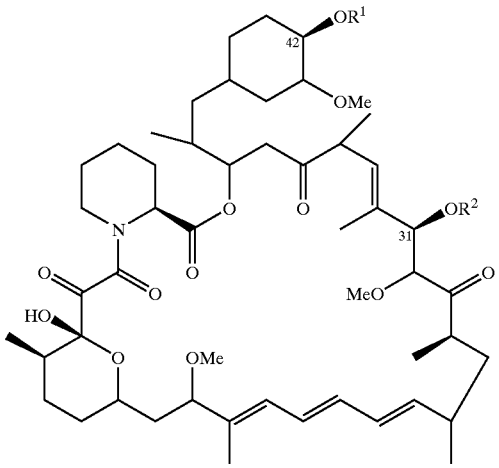

wherein

R¹ and R² are each, independently, hydrogen or —CO(CR³R⁴)_b(CR⁵R⁶)_dCR⁷R⁸R⁹;

R³ and R⁴ are each, independently, hydrogen, alkyl of 1–6 carbon atoms, alkenyl of 2–7 carbon atoms, alkynyl of 2–7 carbon atoms, trifluoromethyl, or —F;

R⁵ and R⁶ are each, independently, hydrogen, alkyl of 1–6 carbon atoms, alkenyl of 2–7 carbon atoms, alkynyl of 2–7 carbon atoms, —(CR³R⁴)_fOR¹⁰, —CF₃, —F, or —CO₂R¹¹;

R⁷ is hydrogen, alkyl of 1–6 carbon atoms, alkenyl of 2–7 carbon atoms, alkynyl of 2–7 carbon atoms, —(CR³R⁴)_fOR¹⁰, —CF₃, —F, or —CO₂R¹¹;

R⁸ and R⁹ are each, independently, hydrogen, alkyl of 1–6 carbon atoms, alkenyl of 2–7 carbon atoms, alkynyl of 2–7 carbon atoms, —(CR³R⁴)_fOR¹⁰, —CF₃, —F, or —CO₂R¹¹;

R¹⁰ is hydrogen or —COCH₂—S—CH₂CH₂—(O—CH₂—CH₂)_n—OCH₃;

R¹¹ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that R¹ and R² are both not hydrogen and further provided that either R¹ or R² contains at least one —(CR³R⁴)_fOR¹⁰ group in which R¹⁰ is —COCH₂—S—CH₂CH₂—(O—CH₂—CH₂)_n—OCH₃, or a pharmaceutically acceptable salt thereof.

16. A pharmaceutical composition which comprises a compound having the structure

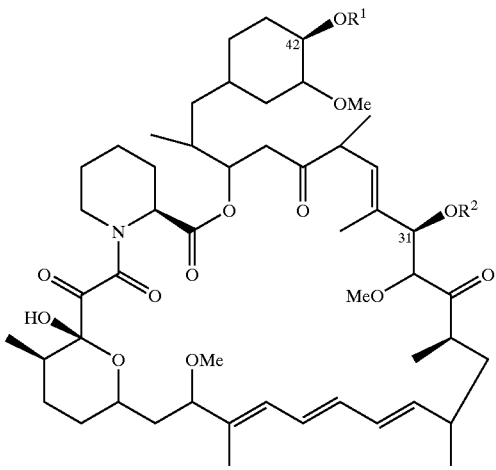

wherein

R¹ and R² are each, independently, hydrogen or —CO(CR³R⁴)$_b$(CR⁵R⁶)$_d$CR⁷R⁸R⁹;

R³ and R⁴ are each, independently, hydrogen, alkyl of 1–6 carbon atoms, alkenyl of 2–7 carbon atoms, alkynyl of 2–7 carbon atoms, trifluoromethyl, or —F;

R⁵ and R⁶ are each, independently, hydrogen, alkyl of 1–6 carbon atoms, alkenyl of 2–7 carbon atoms, alkynyl of 2–7 carbon atoms, —(CR³R⁴)$_f$OR¹⁰, —CF₃, —F, or —CO₂R¹¹;

R⁷ is hydrogen, alkyl of 1–6 carbon atoms, alkenyl of 2–7 carbon atoms, alkynyl of 2–7 carbon atoms, —(CR³R⁴)$_f$OR¹⁰, —CF₃, —F, or —CO₂R¹¹;

R⁸ and R⁹ are each, independently, hydrogen, alkyl of 1–6 carbon atoms, alkenyl of 2–7 carbon atoms, alkynyl of 2–7 carbon atoms, —(CR³R⁴)$_f$OR¹⁰, —CF₃, —F, or —CO₂R¹¹;

R¹⁰ is hydrogen or —COCH₂—S—CH₂CH₂—(O—CH₂—CH₂)$_n$—OCH₃;

R¹¹ is hydrogen, alkyl of 1–6 carbon atoms, alkenyl of 2–7 carbon atoms, alkynyl of 2–7 carbon atoms, or phenylalkyl of 7–10 carbon atoms;

b=0–6;
d=0–6;
f=0–6;
n=5–450;

with the proviso that R¹ and R² are both not hydrogen and further provided that either R¹ or R² contains at least one —(CR³R⁴)$_f$OR¹⁰ group in which R¹⁰ is —COCH₂—S—CH₂CH₂—(O—CH₂—CH₂)$_n$—OCH₃, or a pharmaceutically acceptable salt thereof, and a pharmaceutical carrier.

17. A compound which is rapamycin 42-ester with 3-hydroxy-2-(2-iodo-acetoxymethyl)-2-methyl-propionic acid.

18. A compound which is rapamycin 42-ester with 3-(2-Iodo-acetoxy)-2-(2-iodo-acetoxymethyl)-2-methyl-propionic acid.

* * * * *